United States Patent [19]

Issenmann

[11] Patent Number: 4,798,805
[45] Date of Patent: Jan. 17, 1989

[54] APPARATUS AND PROCESS FOR PYROLYSIS AND ANALYSIS OF SAMPLES CONTAINING ORGANIC MATTER

[75] Inventor: Olivier Issenmann, Lamorlaye, France

[73] Assignee: Geoservices, Societe Anonyme, Paris, France

[21] Appl. No.: 845,684

[22] Filed: Mar. 28, 1986

[30] Foreign Application Priority Data

Apr. 5, 1985 [FR] France ................. 85 05308

[51] Int. Cl.[4] ................. G01N 25/00; G01N 31/12; G01N 33/24
[52] U.S. Cl. ...................... 436/157; 422/54; 422/80; 436/32; 436/143; 436/145; 436/154; 436/160
[58] Field of Search ............... 422/54, 78, 80; 436/32, 436/31, 59, 154, 155, 157, 160, 139, 143, 145, 146

[56] References Cited

U.S. PATENT DOCUMENTS

| | | |
|---|---|---|
| 3,296,435 | 1/1967 | Teal et al. ................. 422/78 |
| 3,953,171 | 4/1976 | Espitalie et al. ................. 436/143 X |
| 3,972,682 | 8/1976 | Stephens et al. ................. 422/78 |
| 3,985,509 | 10/1976 | Trone et al. ................. 422/54 |
| 4,023,929 | 5/1977 | Becker et al. ................. 422/78 |
| 4,116,632 | 9/1978 | Kaartinen et al. ................. 436/59 |
| 4,153,415 | 5/1979 | Espitalie et al. ................. 422/80 X |
| 4,213,763 | 7/1980 | Madec et al. ................. 436/160 |
| 4,229,181 | 10/1980 | Espitalie et al. ................. 436/155 X |
| 4,244,917 | 1/1981 | Woods et al. ................. 436/155 |
| 4,311,664 | 1/1982 | Zaremba et al. ................. 436/160 |
| 4,462,963 | 7/1984 | O'Brien et al. ................. 422/78 |
| 4,518,699 | 5/1985 | Bohl ................. 436/139 X |
| 4,519,983 | 5/1985 | Espitalie et al. ................. 436/160 |

Primary Examiner—Barry S. Richman
Assistant Examiner—Robert J. Hill, Jr.
Attorney, Agent, or Firm—Wenderoth, Lind & Ponack

[57] ABSTRACT

An apparatus for analysis of samples containing organic matter, especially of rock from oil drilling mud, including a loading arm hinged at its base to be movable from a tilted position when it receives a sample-bearing cartridge, which fits on the top of the arm, to a vertical position in which the arm can be raised to fit the upper end of the cartridge within a selectively electrically heated and air cooled chamber. A channel for carrier gas, e.g. hydrogen, passes up the arm so that gas passes through the cartridge when it is held in the heating and cooling chamber, and through the heating and cooling chamber and then through a conduit to a burner within an ignition an analysis chamber.

In use, the container is heated to pyrolyze the sample and the resultant vapors are entrained in the gas, burnt and analyzed by flame ionization. After which the sample-bearing cartridge is cooled in the heating and cooling chamber.

20 Claims, 5 Drawing Sheets

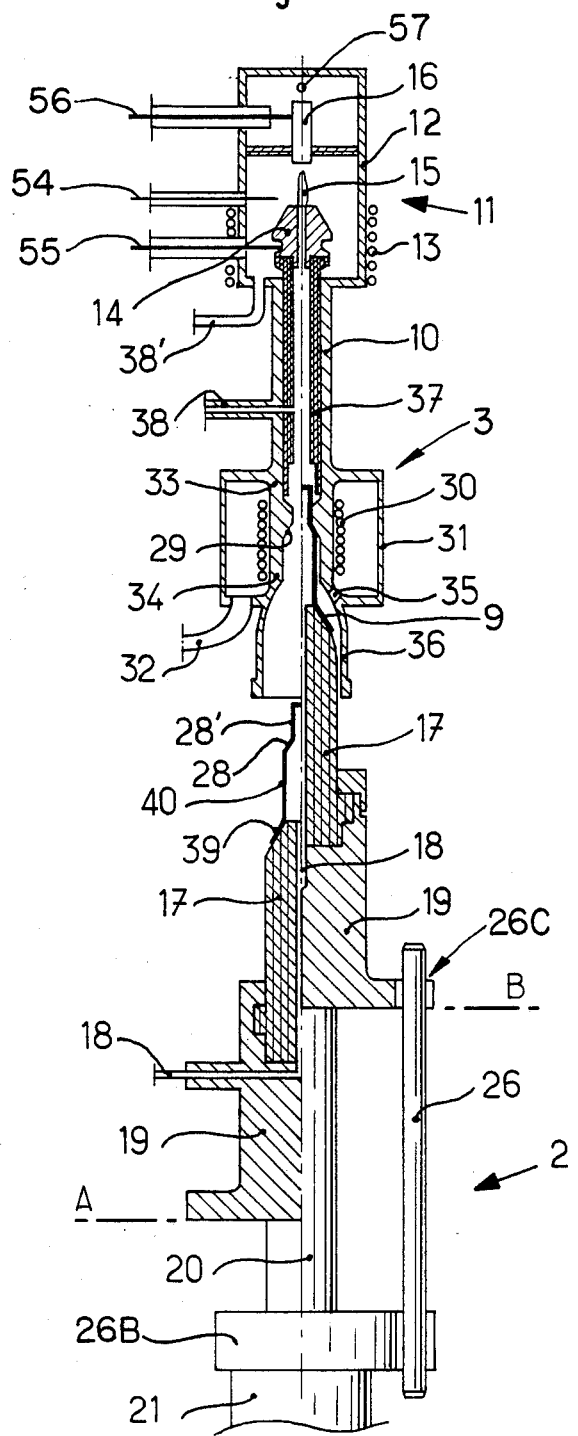

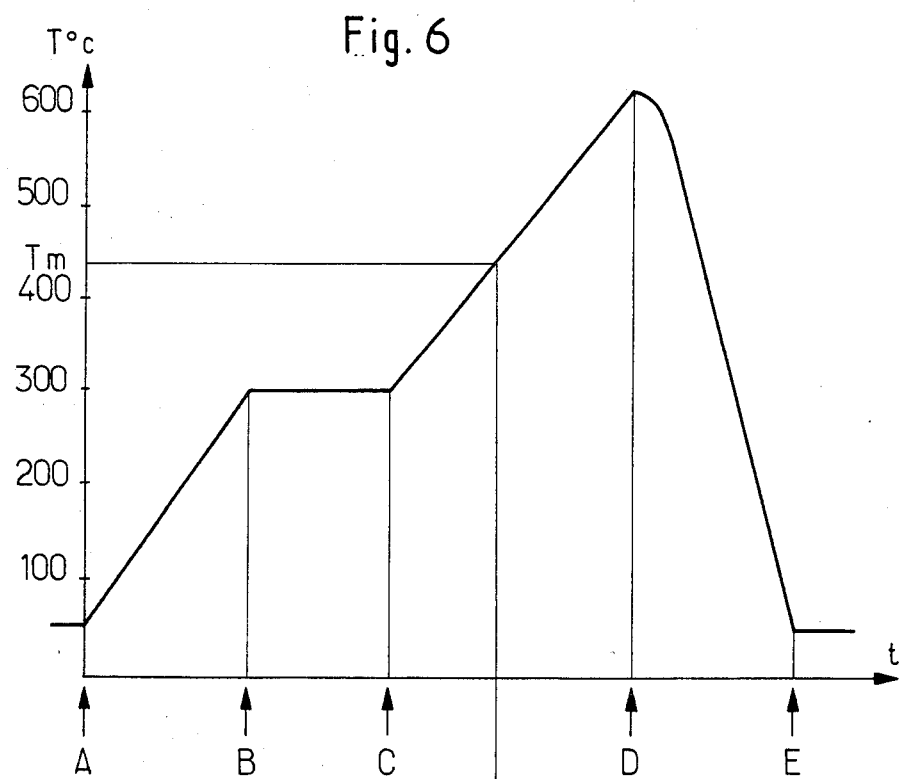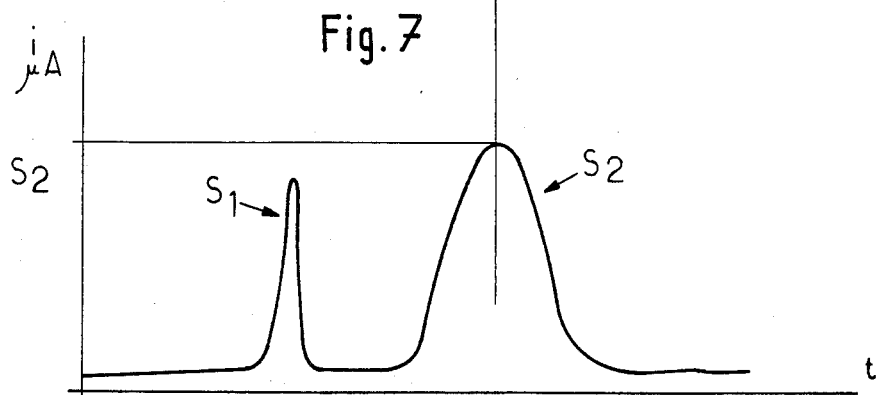

APPARATUS AND PROCESS FOR PYROLYSIS AND ANALYSIS OF SAMPLES CONTAINING ORGANIC MATTER

BACKGROUND OF THE INVENTION

This invention relates to apparatus and a process for the pyrolysis and analysis of samples of material, especially of rock particles, containing organic matter, and to the combination of such apparatus and at least one suitable container for holding each sample within the apparatus during the process.

During exploratory drilling for oil, it is necessary to analyze samples of the rock particles brought up in the drilling mud to determine the proportion of organic matter in the rock. Hitherto this has been done by collecting a sample, e.g. in a sedimentation device, placing the sample of the rock particles in a vessel (dish, boat or crucible) within a heated electric pyrolysis furnace, passing a suitable inert carrier gas (helium or nitrogen) over the sample, and analyzing the resultant gaseous samples derived at various temperatures from the pyrolysis of the organic matter in the rock. Thus, upon testing successive samples from different drilling levels, the presence of oil or gas can be detected.

In the known apparatus for this process, only part of the inert gas passes over the sample and the remainder of the gas flows between the vessel and the furnace wall, which is wasteful of the gas. Also, gaseous by-products are generated by contact of the carrier gas with a metallic interior of the furnace and gas supply pipes, and these by-products may cause faulty analysis of the test results. Great care must be taken so that the operator's fingers do not touch the vessel holding the sample since the resultant deposit of grease from the skin would seriously distort the results, therefore forceps or tweezers have been used in the past. Furthermore, there is a waste of heat energy since the vessel holding the sample is heated inefficiently by radiation from the inside of the furnace, and there can be a significant difference between the recorded temperature of the furnace and that of the sample which leads to uncertainty in consideration of the analyses.

It is an object of the invention to provide an apparatus and a method which substantially overcome these disadvantages and which provide a rapid, precise and accurate analysis of samples containing organic material, especially of particles of rock in a drilling mud. We have devised an apparatus wherein the sample is held in a chamber which is of limited capacity, i.e. not greatly larger in size than the sample, the container is placed in direct thermal contact with a heating means which surrounds the container of sample, and the gas used to carry the gaseous pyrolysis products passes through the container and directly to an analysis station.

Preferably the apparatus does not contain metallic parts in contact with the hot gas stream.

SUMMARY OF THE INVENTION

According to the present invention we provide an apparatus for the pyrolysis and analysis of samples containing organic matter, which comprises a device for heating a heat-resistant cartridge containing a sample to be analyzed, while the cartridge is held in contact with said device, means for cooling the heating device after it has been heated, a conduit for conducting vapors from the cartridge, while it is in contact with the heating device, to an ignition and analysis chamber, means for supply of a gas to an inlet of said cartridge such that the gas passes through the cartridge and then through said conduit so as to entrain said vapors, means for igniting a flame of a burner at the end of the conduit within the analysis chamber, means for analyzing the chemical composition of the flame and for recording the results of the analysis, and means for transferring a cartridge holding the sample into contact with said heating device.

Preferably the transfer means comprises an arm hinged at its lower end with the upper end of the arm being shaped to receive the lower end of a cartridge holding the sample, means for moving said arm from a vertical position beneath the heating device to a tilted or inclined position wherein its upper end is outside the apparatus, and means for raising the upper end of the arm when the arm is in a vertical position.

In addition, the heating device preferably comprises a tube having an open end which is tapered conically so as to receive a corresponding conically tapering neck of the sample-containing cartridge to be inserted therein.

Each cartridge used with such apparatus is appropriately shaped so as to fit at its upper end within the heating device and at its lower end so as to be supported on the upper end of the transfer means.

The process of the present invention is carried out with the aforesaid apparatus in which a sample to be analyzed is placed in a cartridge supported within the already heated heating device, the cartridge is left in position for a time to allow the sample to become heated by conduction through the walls of the cartridge, hydrogen gas is supplied through the chamber, oxygen-containing gas is supplied to te combustion chamber and the gaseous mixture containing pyrolysis products from the rock sample is burned and the flame is analyzed.

The invention will be described with reference to the analysis of samples, e.g. of 100 mg size, of rock particles from drilling mud, although it might be applied to other organic-containing samples.

The invention will be described in detail with reference to a preferred embodiment of the apparatus thereof.

BRIEF DESCRIPTION OF THE DRAWINGS

FIG. 2 is a vertical axial diagrammatic section of the means for loading the sample-containing cartridge and for heating and cooling it, and associated gaseous transport means, the lower part of the apparatus being shown on the left-hand side of the figure in its lower position and on the right-hand side in its raised operative position;

FIGS. 6 and 7 are graphs illustrating respectively the temperatures recorded during pyrolysis of a sample in the apparatus of FIG. 1, and the corresponding variation of concentration of hydrocarbons detected by the analysis.

DETAILED DESCRIPTION OF THE INVENTION

Figure 1:
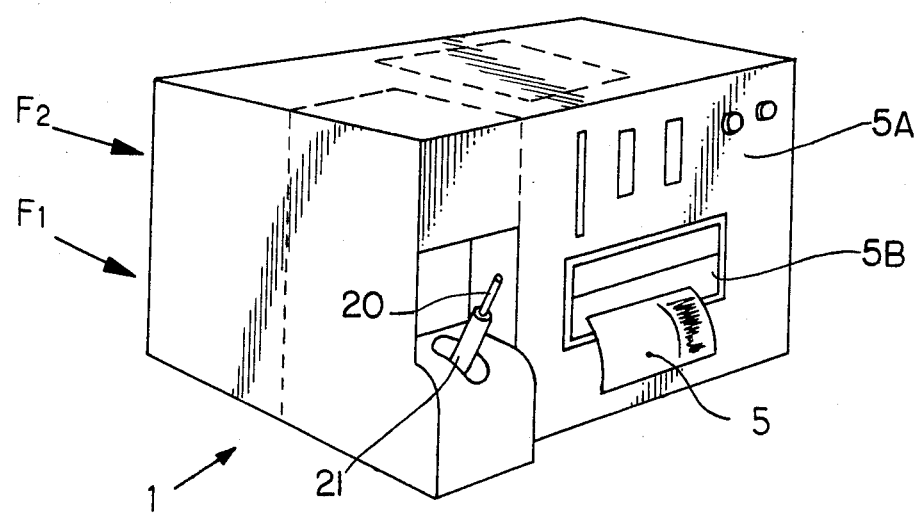
FIG. 1 is a perspective view of the entire apparatus within its external casing, and showing separately therebelow an internal portion, namely in FIG. 1a the device for loading the sample-containing cartridge and for heating the cartridge.
Figure 1A:
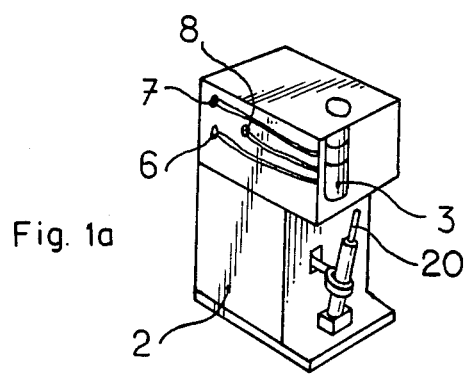

Referring to FIG. 1, it is seen that the apparatus of the invention is enclosed in a casing 1, generally parallelepiped in shape, the front of which displays monitoring and control means indicated as 5A and an aperture 5B from which a continuous sheet 5 emerges bearing a trace showing the analysis record. To the left of this sheet projects an extendible rod 20 of a pivotable cylinder 21 for receiving a removable sample-bearing cartridge 9 (FIG. 2) on the end of the rod. The positions at which air and electric power are supplied to the rear of the casing are indicated by arrows F1 and F2, respectively, A sample-bearing cartridge supporting and transferring means 2 seen in FIG. 1A is located beneath a heating and cooling means 3, which is supplied by electric leads 6 and 7 and protected by a ground wire 8. A conventional hydrogen generating device (not shown) can be located in any convenient part of the casing 1, e.g. beneath the central broken-line square shown on top of the casing.

Figure 3:
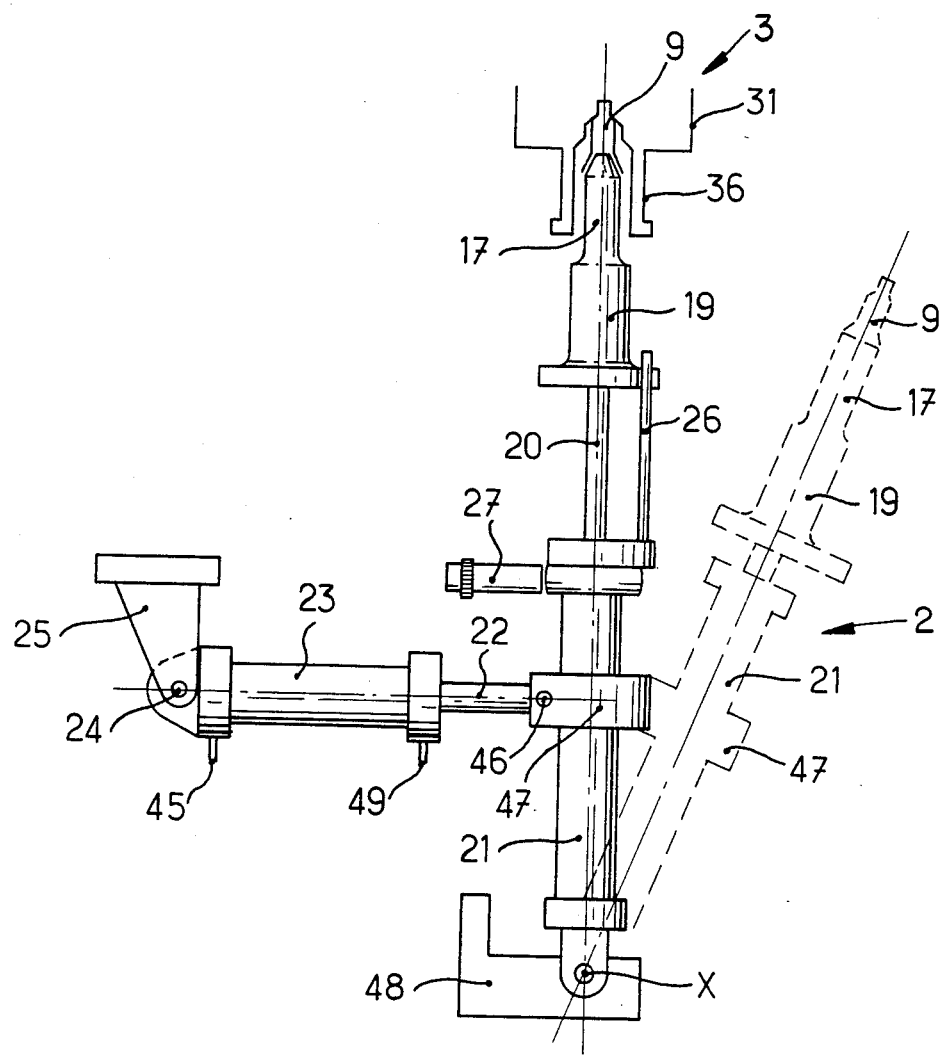
FIG. 3 is an enlarged diagrammatic view, taken in a plane at 90° to the plane of the section of FIG. 2, showing other associated parts of the components of FIG. 2, the cooling device in its loading position being shown in solid lines, and to the right of the drawing in its preloading position in phantom, and the cooling means being shown in a modified shape to that of FIG. 2.

FIGS. 2 and 3 show essential parts of the apparatus of the invention, comprising the supporting and transferring means 2 for loading a sample-bearing cartridge 9 (shown in more detail in FIG. 4), the heating and cooling means 3 of FIG. 1 and an ignition and analysis means 11 (shown in more detail in FIG. 5) connected to the cartridge by conduit means, such as an axial tube 10.

The body of the supporting and transferring means comprises the cylinder 21 having a lower part which pivots about a horizontal axis X (which extends perpendicular to the plane of FIG. 3), and the upper part of which supports a seat 19 on which is disposed a nozzle 17. The nozzle 17 has a central axial channel 18 therethrough which is connected to a valve (not shown) which together comprise a carrier gas supply means for supply of carrier gas for analysis (e.g. from the hydrogen generator). The elements 20, 21, 19, 17 thus described comprise a loading arm which is hinged at its base at the axis X, so as to be movable from the vertical position shown in solid lines to an inclined position shown in phantom in FIG. 3, by means of the reciprocatable action of a horizontal rod 22 which travels within a double acting horizontal actuator or cylinder 23 under the action of hydraulic fluid injected into either a connection shown at 45 or 49, respectively. The hydraulic cylinder 23 is hinged at 24 to a supporting bracket 25 which is mounted inside the casing 1 (FIG. 1). The entire loading arm is pivotally supported about the axis X by means of a bracket 48 mounted on the floor of the casing 1. An adjustable stop 27, also mounted on the casing 1, limits the movement of the loading arm about the axis X, so that in its vertical position as in FIG. 2 it is correctly located beneath a shield or skirt 36 and a sample heating and cooling chamber 31 (described below). The rod 22 is hingedly connected at 46 to a flange 47 connected to the actuator 21.

In its operative vertical position, the elements of the loading arm comprising the nozzle 17, the seat 19 and the rod 20 and are also movable vertically from a lower position shown at A in FIG. 2 to an upper position shown at B in FIG. 2, between the two positions shown respectively at the left and right hand sides of the lower part of FIG. 2, by means of the extendible rod 20 which reciprocates within the cylinder 21 by means of another hydraulically actuated means (the fluid inlets of which are not shown). The vertical movement of the nozzle 17 and seat 19 is guided by an arm 26 fixed to a flange 26B mounted at the top of the actuator 21 and the arm 26 is received in a hole 26C at the base of the seat 19.

Referring now to the upper part of FIG. 2, the heating and cooling means of FIG. 1 is shown comprising a heater 30 and a chamber 31, adapted to be cooled by suitable means, surrounding a central heating pipe 33 which includes a conical section 29 at a lower end thereof to receive the cartridge 9 (only half of which is shown in a heavy line on the right-hand side of FIG. 2), around which pipe 33 is wrapped an electrical resistance heater 30. An inlet 32, adapted to be connected to the air supply shown at F1 in FIG. 1, is provided to admit air through the floor of the chamber 31. The lower end of the pipe 33 is expanded to form a shield or skirt 36 which is shown in FIG. 2 as of bell-shape, but which can also be cylindrical as shown in FIG. 3, is provided beneath the chamber 31 and an aperture 35 allows air to pass from the chamber 31 out through the shield 36 to cool the sample-bearing cartridge 9. A small hole is formed, e.g. at 34 in the pipe 33, to allow the placing of a thermometric or thermal probe connected to a scale shown generally at 5A on the front of the casing 1.

Figure 5:
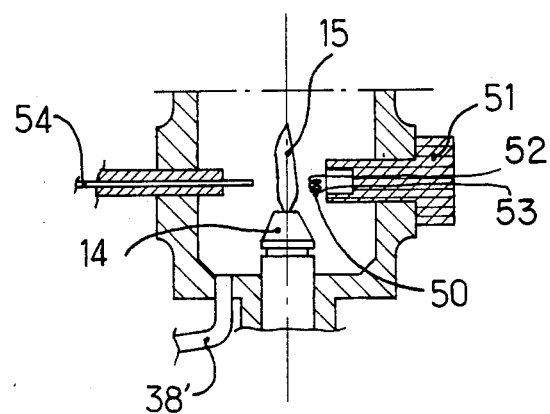
FIG. 5 is an enlarged axial sectional view of the ignition and flame control systems of the analysis portion of the apparatus of FIGS. 1 to 3.

Above the chamber 31 is the conduit means comprising the axial tube 10 which has a heat resistant lining 37 therein, and a lateral inlet 38 is connected to the tube 10 for the supply of an auxiliary carrier gas for the analysis, the tube 10 leading from the top of the cartridge 9 to a burner 14 of the ignition and analysis means 11 (at the top of FIG. 2). The burner is within an ionization chamber 12 surrounded by another resistance heater 13, and above the burner is a flue 16 which communicates the combustion gases into an upper part of the ionization chamber 12 from which the gases escape through a small hole or aperture 57. A thin metallic covering (not shown separately) is provided for the burner 14 and serves as an emitting electrode and the flue 16 is metallic and serves as the corresponding collecting electrode for the purpose of the gas ionization analysis, these electrodes being provided with current by the insulated leads 55 and 56 which are connected to a conventional analysis device which in turn is connected to an instrument for recording the analysis on the paper sheet or tape 5 as shown in FIG. 1. Referring to FIG. 5, further elements within the ignition and analysis means of FIG. 2 are shown, namely ignition means for igniting a flame comprising a filament coil 50 of an ignition spark plug 51 fed by electrical conductors 52 and 53, for ignition of a flame 15 of the burner 14 and means for detecting the presence of a flame at the burner comprising a fiber optic conductor 54 which monitors the presence of the flame and which is connected to a switch (not shown) for the conductors 52 and 53 deactivating the ignition means when a flame is present at the burner.

Figure 4:
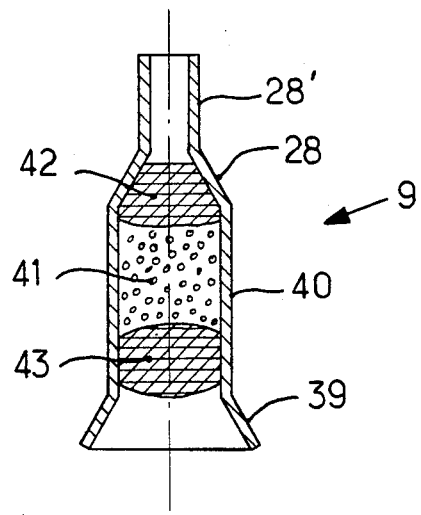
FIG. 4 is an enlarged axial sectional view of a loaded sample-containing cartridge.

FIG. 4 shows details of a container for holding a sample, namely a cartridge 9, suitable for use in the described apparatus. The cartridge has a central tubular body 40 having a tapered recess inside a lower outwardly tapering flange 39, and the upper portion of the body tapers inwardly at 28 to form an outer flange which terminates in a narrower neck 28'. Within the cartridge are upper and lower removable filter pads 42, 43, e.g. of ceramic wool, which retain particles of a sample 41 of rock to be analyzed, while the pads allow passage of gas through the cartridge. Thus, a plurality of cartridges can be used with the device and method according to the present invention.

With respect to the construction materials, preferably the cartridge 9 is made of a heat-conductive copper and the adjacent heating pipe 33 is of stainless steel. The burner jet 14, nozzle 17 and liner 37 of the tube 10 should all be made of ceramic or other heat resistant material which is not affected by the hot gases, so that no high temperature reaction takes place with metallic parts of the apparatus which would contaminate the gases being analyzed.

The operation of the apparatus will now be described. With the loading arm formed by elements 20, 21, 19, 17 in its tilted or inclined position, as shown in phantom on the right-hand side of FIG. 3, the operator removes any cartridge which has just been analyzed, and places a cartridge 9 containing a fresh sample 41 upon the nozzle 17 and seat 19 after which a switch (not shown) is actuated to move the rod 22 of the horizontal hydraulic cylinder 23 so that the arm and cartridge are swung to the vertical position shown to the left in FIG. 2, within the casing 1 and against the stop 27. A further switch is then actuated to cause the vertical actuator comprising the hydraulic cylinder 21 and rod 20, to raise the cartridge 9 until its upper flange 28 is within the heating pipe 33. The pipe 33 is preheated by the electrical resistance heater 30 to a temperature which allows rapid conductive heating of the adjacent cartridge 9. The temperature of the pipe 33 is monitored by a thermal probe placed in the aperture 34 and is thermostatically controlled by the amount of current supplied to the electrical resistance heater 30. The wall of the cartridge 9 is highly heat-conductive, so it is assumed that the temperature of the rock particles 41 is substantially the same as that determined by the probe at 34. Carrier gas for use in the analysis, usually hydrogen from the hydrogen generating device, is injected through the channel 18 and upwards through the nozzle 17, and the gas passes through the filter pads 42, 43 within the cartridge 9 and entrains the vaporized products given off by the heated rock. The gaseous mixture passes through the conduit formed by the axial tube 10 and the resistant lining 37 and, together with any auxiliary gas (50% of the total gas flow) injected at inlet 38 into the burner 14, is burned when the flame 15 has been formed by a spark from the ignition spark plug 51. The waste gases escape through the hole 57. An electrical potential is applied across the ionization electrodes in the chamber 12, whereby each carbon atom passing through the flame is ionized and a corresponding electric current passes between the electrodes formed by the coating on the burner 14 and the flue 16. The results of the analysis are transcribed onto the paper sheet 5. Air for the combustion is supplied through the conduit 38'.

A particular preferred way of carrying out the analysis process is further described with reference to the graph shown in FIGS. 6 and 7. The initial heating of the electrical resistance heater 30 is at a linear rate, see stage A to B of FIG. 6, until a temperature of 300° C., detected by the probe at 34, is reached, upon which heating is stopped for a period corresponding to the plateau B-C, to allow heat transfer to the heating pipe within the chamber 31. At the end of this period, the rod 20 of the hydraulic cylinder 21 raises the cartridge 9 into contact with the heater 3, a valve is opened electrically to allow hydrogen gas to enter the channel 18, after which the filament coil 50 of the ignition spark plug 51 is electrically heated until the flame 15 is lit and the fiber optic conductor 54 signals the presence of the flame to a photo-diode (not shown) which is connected to a switch which switches off the current to the ignition spark plug 51. The resistance heater 13 around the ionization chamber 12 is also electrically heated to a suitable temperature.

Current is again supplied to the electrical resistance heater 30 so that heating proceeds at a linear rate again until a prescribed maximum temperature of 600° C. as detected by the thermal probe is reached in the heating chamber 3. Heating is then stopped and air is supplied through the inlet 32 to cool the heating chamber 3 until the probe indicates that the temperature has fallen to 50° C. The cooling air and hydrogen gas supply are then cut off, whereupon the flame 15 is extinguished. The operator then hydraulically lowers the rod 20 and hydraulically tilts the arm outward to an inclined position so that the cartridge 9 can be removed. If desired, a further cartridge may then be put in place and its sample analyzed.

The following types of reactions take place during the different temperatures of this process.

(A) From 100° to 300° C., all the hydrocarbons contained in the gas and oil in the rock sample are vaporized and extracted and entrained in the hydrogen carrier gas;

(B) From 400° to 600° C., and while the carrier gas is free of oxygen, a fraction (known as "kerogen") of the organic matter in the sample is pyrolyzed into hydrocarbons which are also vaporized and entrained in the carrier gas;

(C) From 500° to 600° C., if the carrier gas is replaced by pure oxygen, the residual unoxidized organic matter in the rock is oxidized and transformed essentially into carbon dioxide gas and water vapor.

Each of the gases produced can then be qualitatively and quantitatively analyzed.

For stage (C), an external supply of oxygen gas is connected to the inlet channel 18 in place of the hydrogen, by turning an appropriate valve (not shown). In this case, the entire flame ionization apparatus may be replaced by an apparatus for the detection and measurement of carbon dioxide receiving the input from tube 10 of the apparatus.

The analysis by means of the flame ionization detection and analysis station will then sccessively measure the quantities of organic carbon which correspond to (a) the natural hydrocarbons present in rock samples; (b) the natural hydrocarbons produced by the pyrolysis of the "kerogen" fraction; and (c) the remainder of the non-pyrolyzable organic matter of the rock.

Referring to FIG. 6, the temperatures recorded by the thermal probe and assumed to be the temperatures of the sample are shown on the ordinate, against time on the abscissa. FIG. 7 shows the relative amounts of natural hydrocarbons produced from the sample over the same time scale as in FIG. 6 with a first peak S1 corresponding to the natural hydrocarbons and a second peak S2 corresponding to hydrocarbons formed by pyrolysis of the "kerogen", at the temperature Tm in FIG. 6. The time elapsed between points A and E is 10 to 15 minutes.

The cartridge and adjacent heating means can be modified and could be of a different shape than that shown, for example, the heating chamber could consist of two heating sections which are removable and replaced after the heating stage by two cooling sections which are in turn removable.

The entire process could be computer-controlled.

The invention allows the sample-bearing cartridge to be placed, without contact of the operator's fingers upon the cartridge, into the heater wherein the sample can be heated rapidly at a linear rate up to a temperature of about 600° C. with minimal expenditure of energy.

Helium or nitrogen can be used in place of or in addition to hydrogen as the carrier gas.

Although certain preferred embodiments have been shown and described, it should be understood that many changes and modifications may be made therein without departing from the scope of the appended claims.

I claim:

1. A method for pyrolyzing and analyzing samples containing organic matter, comprising:

loading a sample to be analyzed in a flow through cartridge;

placing a lower end of the sample-bearing cartridge on a supporting and transferring means when the supporting and transferring means is in a cartridge loading position;

actuating the supporting and transferring means to pivot the sample-bearing cartridge in a vertical plane into a position at which the sample-bearing cartridge is aligned with a heating means and moving the sample-bearing cartridge to bring an upper end of the sample bearing cartridge into contact with the heating means;

heating the sample-bearing cartridge with the heating means by conduction of heat through the sample-bearing cartridge;

passing hydrogen gas through a carrier gas supply means disposed in the supporting and transferring means, through the sample-bearing cartridge, through the heating means, through a conduit means into an ignition means which includes a burner, an igniting means, and an analysis means;

igniting a gaseous mixture comprising the hydrogen and pyrolysis products released from the heating step by passing the gaseous mixture through the burner and igniting the gaseous mixture with the igniting means to form a flame at the burner; and analyzing the flame with the analysis means to measure the quantitites of organic matter therein.

2. The method of claim 1, wherein the heating means is heated prior to contacting the sample-bearing cartridge therewith and the sample-bearing cartridge is cooled by a cooling means after the flame has been analyzed by the analysis means.

3. The method of claim 1, wherein the sample-bearing cartridge is heated to a first temperature during the heating step, the hydrogen gas passing step is carried out during the heating step, and wherein after the analysis step, the method further comprises terminating the hydrogen gas passing step, then passing oxygen gas through the sample-bearing cartridge while heating the cartridge to a second temperature higher than the first temperature, igniting a second gaseous mixture comprising the oxygen gas and oxidized organic matter from the step of heating the cartridge to the second temperature by passing the second gaseous mixture through the burner and igniting the second gaseous mixture to form a second flame at the burner, and analyzing the second flame withthe analysis means to measure the quantities of carbon dioxide therein.

4. The method of claim 1, wherein the upper end of the sample-bearing cartridge is tapered and the tapered upper end is fitted into the lower end of a tube forming part of the heating means and the lower end of the sample bearing cartridge is tapered and the tapered lower end of the sample-bearing cartridge is supported on a correspondingly tapered part of the support and transferring means.

5. The method of claim 1, wherein the means for supporting and transferring the sample-bearing cartridge includes an extendible arm which is pivotally moved from a vertical position in axisl alignment with the heating means to the cartridge loading position where the arm is in an inclined position not in axial alignment with the heating means when the lower end of the sample-bearing cartridge is to be removed from the supporting and transferring means, and when the sample-bearing cartridge is to be loaded onto the supporting and transferring means the lower end of the sample-bearing cartridge is placed on a free end of the arm when the arm is in the inclined position after which the arm is pivoted to the vertical position and extended from a first position at which the upper end of the sample-bearing cartridge is not in contact with the heating means to a second position at which the upper end of the sample-bearing cartridge is in contact with the heating means.

6. An apparatus for pyrolyzing and analyzing samples containing organic matter, comprising:

a flow through cartridge constructed and arranged for holding a sample therein, said cartridge including a lower end, an upper end, means defining an inlet in the lower end, and means defining an outlet in the upper end;

a casing;

heating and cooling means disposed within said casing;

supporting and transferring means disposed within said casing for removably supporting the lower end of the cartridge and transferring the upper end of the cartridge into and out of engagement with said heating means by pivoting the cartridge in a vertical plane from a loading position to a position in alignment with said heating means and moving the cartridge from a position at which the upper end of the cartridge is not in contact with the heating means to a position at which the upper end of the cartridge contacts the heating means so that the cartridge can be heated by rapid conductive heating;

carrier gas supply means for supplying a carrier gas to the inlet of the cartridge when the cartridge is supported by the supporting and transferring means;

conduit means for passage of vapors from the outlet of the cartridge when the upper end of the cartridge is held by said supporting and transferring means in contact with said heating means; and ignition means in fluid communication with said conduit means for igniting a flame, and analysis means for analyzing the chemical composition of a combusted gas from such a flame and for recording the results of such an analysis.

7. The apparatus of claim 6, wherein said ignition means includes a burner and means for igniting a flame at said burner and said conduit means comprises a tube extending between said heating means and said burner, said tube including means defining an inlet for supplying auxiliary gas to said burner.

8. The apparatus of claim 7, wherein said tube includes an interior lining made of ceramic material.

9. The apparatus of claim 7, wherein said ignition means further includes means for detecting the presence of a flame at said burner and means for deactivating said means for igniting a flame when a flame is present at said burner.

10. The apparatus of claim 6, wherein the upper and lower ends of the cartridge are tapered, the tapered lower end and tapered upper end each having a cross-section which becomes smaller in an axial direction towards the upper end of the cartridge.

11. The apparatus of claim 10, wherein said cartridge includes at least two heat-resistant, gas-permeable removable pads therein for retaining a sample to be analyzed within said cartridge and said cartridge is made of a heat-conductive material.

12. The apparatus of claim 10, wherein the cartridge includes a central tubular body extending in the axial direction between the tapered upper and lower ends thereof and a cylindrical neck extending in the axial direction from the tapered upper end of the cartridge.

13. The apparatus of claim 6, wherein said heating means comprises a pipe having an end constructed and arranged to receive the upper end of the cartridge when the upper end of the cartridge is held in contact with said heating means by said supporting and transferring means.

14. The apparatus of claim 13, wherein said heating means further comprises a resistance heater disposed around said end of said pipe.

15. The apparatus of claim 13, wherein said cooling means comprises means defining a chamber disposed around said end of said pipe, means defining an inlet into said chamber for supplying cooling gas thereto and means defining an aperture through said end of said pipe for passing cooling gas from said chamber to an outer surface of the cartridge when the upper end of the cartridge is in contact with said heating means to thereby cool the cartridge when the upper end of the cartridge is in contact with said heating means to thereby cool the cartridge after heating thereof by said heating means.

16. The apparatus of claim 15, wherein said heating means further comprises a shield extending from said end of said tube so as to surround the lower end of the cartridge when the upper end of the cartridge is held in contact with said heating means by said supporting and transferring means.

17. The apparatus of claim 6, wherein said supporting the transferring means comprises an extendible arm which is pivotally mounted in said casing for movement from a vertical position in axial alignment with said heating means to an inclined position not in axial alignment with said heating means, said arm having a free end for supporting the lower end of the cartridge, and when the cartridge is mounted on the free end of the arm and the arm is in its vertical position, said arm being extendible from a first position at which the upper end of the cartridge is not in contact with said heating means to a second position at which the upper end of the cartridge contacts said heating means.

18. The apparatus of claim 17, wherein said carrier gas supply means comprises means defining a channel extending axially through said arm for passing carrier gas therethrough and into the cartridge when the cartridge is mounted on said free end of said arm, the means defining the channel being constructed and arranged for connection to a supply of carrier gas.

19. The apparatus of claim 18, wherein said free end of said arm is tapered for fitting in a correspondingly shaped tapered recess in the lower end of the cartridge and said channel extends axially through said tapered free end of said arm.

20. The apparatus of claim 19, wherein said tapered free end of said arm is made of ceramic material.

* * * * *